United States Patent
Boggs et al.

(10) Patent No.: US 9,962,478 B2
(45) Date of Patent: *May 8, 2018

(54) SYSTEMS AND METHODS FOR ACHIEVING TARGET POST-PROCEDURE FRACTION OF CELLS REMAINING, HEMATOCRIT, AND BLOOD VOLUME DURING A THERAPEUTIC RED BLOOD CELL EXCHANGE PROCEDURE WITH OPTIONAL ISOVOLEMIC HEMODILUTION

(71) Applicant: Fenwal, Inc., Lake Zurich, IL (US)

(72) Inventors: Daniel R. Boggs, Libertyville, IL (US);
Kyungyoon Min, Kildeer, IL (US);
Lan T. Nguyen, Vernon Hills, IL (US);
John T. Foley, Wheeling, IL (US);
Brian C. Case, Lake Villa, IL (US)

(73) Assignee: Fenwal, Inc., Lake Zurich, IL (US)

(*) Notice: Subject to any disclaimer, the term of this patent is extended or adjusted under 35 U.S.C. 154(b) by 114 days.

This patent is subject to a terminal disclaimer.

(21) Appl. No.: 15/184,492

(22) Filed: Jun. 16, 2016

(65) Prior Publication Data

US 2016/0296688 A1   Oct. 13, 2016

Related U.S. Application Data

(62) Division of application No. 13/840,113, filed on Mar. 15, 2013, now Pat. No. 9,393,359.

(Continued)

(51) Int. Cl.
*A61M 1/34* (2006.01)
*A61M 1/38* (2006.01)
*A61M 1/36* (2006.01)

(52) U.S. Cl.
CPC .......... *A61M 1/3455* (2013.01); *A61M 1/342* (2013.01); *A61M 1/3437* (2014.02);
(Continued)

(58) Field of Classification Search
CPC .. A61M 1/342; A61M 1/3437; A61M 1/3455; A61M 1/3458; A61M 1/3496;
(Continued)

(56) References Cited

U.S. PATENT DOCUMENTS 5,868,696 A   2/1999   Giesler et al.
6,027,657 A   2/2000   Min et al.
(Continued)

OTHER PUBLICATIONS

Cobe Spectra Apheresis System, Therapeutic Apheresis Guide, Red Blood Cell Exchange (RBCX) Procedure, pp. 4-1 through 4-21.
(Continued)

*Primary Examiner* — Benjamin Klein
(74) *Attorney, Agent, or Firm* — Cook Alex Ltd.

(57) ABSTRACT

Systems and methods for performing a therapeutic red blood cell exchange procedure are disclosed. In one aspect, a system includes a first flow path for flowing whole blood from a patient. A separator communicates with the first flow path for separating at least red blood cells from plasma. Second and third flow paths communicate with the separator for respectively flowing the separated plasma and red blood cells from the separator. A flow controller is associated with the flow paths to control fluid communication between the flow paths. The controller is configured to perform the procedure to achieve a target fraction of patient cells remaining, target hematocrit, and a target patient fluid volume change at the completion of the procedure based on data input by the operator.

12 Claims, 7 Drawing Sheets

Related U.S. Application Data

(60) Provisional application No. 61/622,113, filed on Apr. 10, 2012.

(52) U.S. Cl.
CPC ........ *A61M 1/3458* (2014.02); *A61M 1/3496* (2013.01); *A61M 1/3672* (2013.01); *A61M 1/38* (2013.01); *A61M 1/385* (2013.01); *A61M 2205/3334* (2013.01); *A61M 2205/505* (2013.01); *A61M 2205/52* (2013.01); *A61M 2230/005* (2013.01); *A61M 2230/207* (2013.01)

(58) Field of Classification Search
CPC ...... A61M 1/3672; A61M 1/38; A61M 1/385; A61M 2205/3334; A61M 2205/505; A61M 2230/005; A61M 2230/207
See application file for complete search history.

(56) References Cited

U.S. PATENT DOCUMENTS

| | | |
|---|---|---|
| 6,451,203 B2 | 9/2002 | Brown |
| 6,802,982 B2 | 10/2004 | Brown |
| 9,393,359 B2* | 7/2016 | Boggs ................... A61M 1/342 |
| 2004/0249332 A1 | 12/2004 | Bainbridge et al. |
| 2009/0211987 A1* | 8/2009 | Min ........................ A61M 1/38 210/744 |
| 2010/0168639 A1* | 7/2010 | Cantu ................... A61M 1/342 604/4.01 |

OTHER PUBLICATIONS

EP Appl No. 13162993.3-1651, EPO search report dated Jul. 5, 2013.

* cited by examiner

SYSTEMS AND METHODS FOR ACHIEVING TARGET POST-PROCEDURE FRACTION OF CELLS REMAINING, HEMATOCRIT, AND BLOOD VOLUME DURING A THERAPEUTIC RED BLOOD CELL EXCHANGE PROCEDURE WITH OPTIONAL ISOVOLEMIC HEMODILUTION

BACKGROUND

The present disclosure is directed to the processing and collection of blood and its components. More particularly, the present disclosure is directed to a method of collecting whole blood in a suitable anticoagulant, holding the anticoagulated whole blood for a selected period of time, separating concentrated red blood cells from the previously held whole blood and storing the same.

This disclosure generally relates to a biological fluid processing system and method thereof. More specifically, this disclosure relates to a system and method for a therapeutic exchange procedure that exchanges at least one constituent component, such as a blood component, from a withdrawn biological fluid, such as whole blood, from a patient with one or more replacement fluids that are infused to the patient.

Blood processing systems and methods that relate to a therapeutic exchange procedure typically withdraw a biological fluid, such as whole blood, from a patient. The biological fluid, such as whole blood, may be directed to a separator, such as a centrifugal or membrane assembly, for separation of at least one constituent component, such as at least one blood component, for example, red blood cells, plasma and/or platelets, from the remaining blood components. Depending on the procedure, certain separated constituent components may be retained by the system and not returned to the patient. The remaining separated constituent components may be returned to the patient together with one or more fluids to replace the constituent retained by the system. The particular separated constituent that is not returned to the donor may depend on the specific medical needs of the patient. For example, one type of therapeutic exchange procedure is a red blood cell exchange procedure that removes a quantity of separated red blood cells from the withdrawn whole blood of a patient and returns to the patient at least one replacement fluid, such as red blood cells from a healthy donor, containing an additive solution or other fluid, along with the remaining separated blood components.

In a therapeutic exchange procedure, it is generally desired to achieve a certain target fraction of original patient cells remaining, FCR, in order to reduce the population of diseased cells. It is also desired to maintain a patient's fluid volume such that the difference between the volume of removed fluid and replaced fluid, $\Delta V$, is within a desired range. In a red blood cell exchange procedure it may also be desired to achieve a targeted volume fraction of red blood cells (fractional hematocrit, $H_T$) at the conclusion of the procedure so as to avoid the patient receiving too many or too few replacement red blood cells. A system and method for controlling hematocrit during a therapeutic red blood cell exchange procedure utilizing a hematocrit sensor is disclosed in US 2009/0211987, incorporated herein by reference.

By way of the present disclosure, systems and methods for achieving a target FCR, hematocrit, and fluid volume change during a therapeutic red blood cell exchange procedure are disclosed, as well as systems and methods for performing such a procedure with isovolemic (i.e., without any change in volume) hemodilution.

SUMMARY OF THE DISCLOSURE

The present subject matter has a number of aspects which may be used in various combinations, and the disclosure of one or more specific embodiments is for the purpose of disclosure and description, and not limitation. This summary highlights only a few of the aspects of this subject matter, and additional aspects are disclosed in the drawings and the more detailed description that follows.

In accordance with one aspect of the disclosure, a blood processing system is provided comprising a blood separation device for separating whole blood into a red blood cell component and a plasma component. The system includes an inlet flowpath having a pump operable at a prescribed rate $Q_{WB}$ to convey whole blood from a patient having a whole blood volume V, with a whole blood hematocrit value $H_T$, into the separation device. A return flowpath is provided to convey fluid to the patient, along with a first outlet flowpath including a pump operable at a prescribed flow rate $Q_P$ to convey separated plasma from the separation device. A second outlet flowpath is provided to convey separated red blood cells from the separator. A source of replacement red blood cells having a hematocrit $H_{T1}$ is provided so as to be in fluid communication with the return flowpath. A third flowpath including a pump operable at a prescribed flow rate $Q_{RF}$ is provided to convey replacement red blood cells to the patient. The system also includes a controller including a first stage operable to accept or derive input values relating to the patient condition and clinical objectives; a second stage operable to derive operating values for the for $Q_{WB}$, $Q_P$, and $Q_{RF}$ such that the clinical objective are achieved simultaneously at the end of the procedure; and a third stage operable to maintain and or adjust these values in accordance with changing procedural conditions.

In keeping with another aspect of the disclosure, the first stage of the system is operable to accept or derive at least the following inputs: the target post-procedure fraction of patient cells remaining (FCR), hematocrit ($H_{TF}$), and patient fluid volume change ($\Delta V$); the initial patient fluid volume ($V_0$); the initial patient hematocrit ($H_{T0}$), the hematocrit of the replacement fluid ($H_{T8}$); and the maximum blood draw rate ($Q_{WB, MAX}$).

In a further aspect of the disclosure, the second stage is operable to determine the parameters M and F as follows:

$$M = 1 - \frac{\ln(FCR)}{\ln(1 + \Delta V/V_0)} \quad \Delta V \neq 0$$

and $$F = \frac{H_{T8}}{H_{T0}} \left[ \frac{FCR^{\frac{M}{M-1}} - 1}{FCR^{\frac{M}{M-1}} - \frac{H_{TF}}{H_{T0}}} \right] \quad \Delta V \neq 0$$

$$F = \frac{H_{T8}}{H_{T0}} \quad \Delta V = 0$$

and is then further operable to determine the operating flow rates as follows:

$$Q_{RF} = \frac{M}{F(M-1)} Q_{WB,MAX}.$$

$$Q_P = (F-1) Q_{RF}.$$

In another aspect, the operating flow rates are all adjusted proportionally to not exceed the allowable citrate infusion rate and still maintain the flow rate ratios that will achieve the procedure objectives.

In a further aspect of the disclosure, a method for performing isovolemic hemodilution in a red blood cell exchange procedure for a patient is provided in which a target dilution hematocrit is entered into a blood processing system; a replacement fluid is selected; an amount of whole blood to be processed to achieve the target dilution hematocrit is calculated; whole blood from the patient is processed and replacement fluid is returned to the patient; the amount of whole blood processed or the procedure time to achieve the target dilution hematocrit is monitored; and the processing of whole blood and returning red blood cells to the patient in accordance with a red blood cell exchange procedure is continued to achieve a target end hematocrit. The replacement fluid is preferably selected from one of saline and albumin, or an albumin solution.

In a related aspect, a method for performing isovolemic hemodilution in a red blood cell exchange procedure for a patient is provided in which a target dilution hematocrit is entered; a target dilution volume is entered; a replacement fluid is selected; whole blood from the patient is processed and replacement fluid is returned to the patient; the amount of replacement fluid returned to the patient is monitored until the target dilution volume is attained; and the processing of whole blood and returning red blood cells to the patient in accordance with a red blood cell exchange procedure is continued to achieve a target end hematocrit.

In a further related aspect a method of performing isovolemic hemodilution in a red blood cell exchange procedure for a patient is provided in which a target dilution hematocrit is established; a volume of replacement fluid necessary to achieve the targeted dilution hematocrit is calculated; a first replacement fluid is selected; whole blood is processed and plasma and first replacement fluid are returned to the patient; an amount of first replacement fluid returned to the patient is displayed on a user interface; a second replacement fluid is introduced when the amount of said first replacement fluid displayed on the user interface is equal to the calculated volume of replacement fluid; and the red blood cell exchange procedure is continued until a target end hematocrit is achieved.

In accordance with another aspect the isovolemic hemodilution method may be performed in which the target end hematocrit is achieved by linearly increasing the hematocrit of the replacement red blood cells introduced into the patient over the course of the red blood cell exchange procedure. Alternatively, the target end hematocrit is achieved by exponentially increasing the hematocrit of the replacement red blood cells introduced into the patient over the course of the red blood cell exchange procedure. Further, the second replacement fluid may include red blood cells. In addition, the isovolemic hemodilution may be performed in which return of the first replacement fluid is ceased prior to introducing the second replacement fluid.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

In performing a red blood cell exchange procedure, it is desirable to achieve a target fraction of original patient cells remaining, FCR, in order to reduce the population of diseased cell. It may also be desirable to achieve a target hematocrit, $H_T$, for the patient at the end of the exchange procedure. The target FCR and hematocrit are important in the treatment of diseases such as sickle cell anemia. For this disease, keeping these parameters low is beneficial for maintaining the blood viscosity at an acceptable level. Achieving a target increase or decrease in patient fluid volume, $\Delta V$, is also important for maintaining the patient's blood volume and blood pressure. In accordance with the present disclosure, systems and methods are provided for controlling the blood processing device to remove blood and return replacement fluids so as to simultaneously achieve the end targets for FCR, and hematocrit and fluid volume change. Further, the systems and methods permit such targets to be achieved with isovolemic hemodilution.

Figure 1:
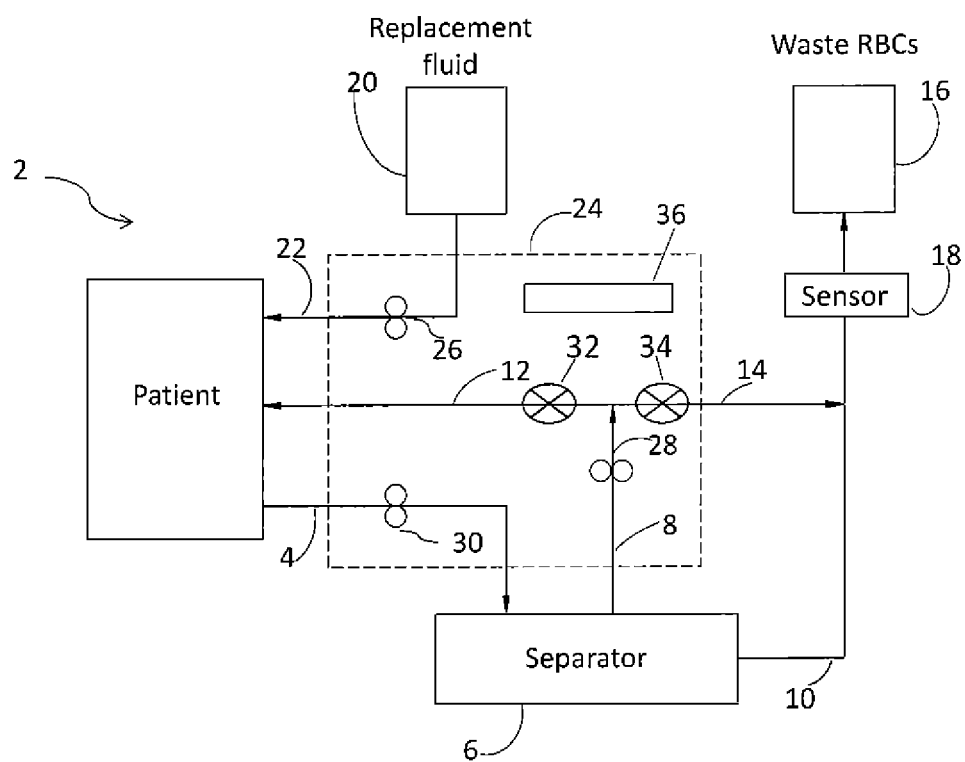
FIG. 1 a diagrammatic view of a preferred system and method in accordance with one embodiment of the subject matter described herein.

In accordance with one embodiment of the present disclosure, FIG. 1 schematically illustrates a processing system, generally indicated at 2, that may be used for processing various fluids in accordance with the subject matter described herein. The system 2 is particularly well suited to processing whole blood and/or other suspensions of biological fluids. Although the processing of whole blood will be described, the illustrated embodiments are not limited to such processing and may be employed for processing other biological fluids. By way of example and not limitation, the systems described herein are particularly suited for a therapeutic red blood cell exchange procedure during which red blood cells are separated from withdrawn whole blood and the remaining blood components and replacement red blood cells alone or with other replacement fluid, such as an additive solution commercially sold under the trademark Adsol®, is returned to a patient. It is understood that the systems described herein are not limited to such procedure and that other procedures are also possible.

In FIG. 1, the system 2 includes a first flow path, generally indicated at 4, that communicates with a patient for flowing (withdrawing) at least a first fluid, such as whole blood, from the patient. In FIG. 1, a separator, generally indicated at 6, may be associated with the first flow path 4 for receiving the whole blood and separating the whole blood from the patient into one or more separated blood components. By way of example, the separator 6 may separate primarily red blood cells from plasma and preferably separates red bloods cells from the remaining blood components, e.g., plasma, platelets and white blood cells. In FIG. 1, a second or plasma flow path, generally indicated at 8, preferably communicates with the separator 6 for flowing the separated plasma and/or other remaining blood components, such as platelets and/or white blood cells, from the separator 6. A third or red blood cell flow path, generally indicated at 10, preferably communicates with the separator 6 for flowing the separated red blood cells from the separator.

The separated plasma may flow from the separator 6 generally in two ways or along two branches of the second flow path 8, such branches generally indicated at 12 and 14. A first branch 12 may communicate, either directly or indirectly with the patient and a second branch 14 may communicate with the red blood cell flow path 10 at a selected location to combine and/or mix with the separated red blood cells.

Also in FIG. 1, a first container or reservoir, generally indicated at 16, is preferably associated with the red blood cell flow path 10, such as at a downstream end of such flow path 10. The first reservoir 16 preferably communicates with the separator 6 to allow the separated red blood cells to flow from the separator 6 to such reservoir 16. A monitoring device, such as a sensor, generally indicated at 18, is optionally associated with the third flow path 10 at a sensing location that is preferably downstream of the selected location where separated plasma in flow path 14 and red blood cells in flow path 10 may combine. In FIG. 1, a second reservoir, generally indicated at 20, may be associated with a source of a replacement fluid, such as fresh red blood cells, and may communicate with the patient, either directly or indirectly, by way of a replacement fluid flow path, generally indicated at 22. While only a single reservoir containing replacement fluid is shown in FIG. 1, the system may advantageously include additional reservoirs containing replacement fluid, as will be described in greater detail below. Although in FIG. 1, the replacement red blood cells flow to the patient separately from the separated plasma, it is also possible for the replacement red blood cells and separated plasma to flow by way of a combined flow path that communicates either directly or indirectly with the patient. As a further option, the system may include a hematocrit sensor.

In FIG. 1, a controller or flow controller, generally indicated at 24, may be associated with one or more flow controlling devices, such as, for example, pumps, generally indicated at 26, 28, and 30, that preferably control the addition of the separated plasma to the separated red blood cells, and valves 32 and 34, for controlling fluid flow through flow paths 12 and 14, respectively. In FIG. 1, pump 28 is preferably associated with flow path 8 for respectively controlling fluid flow of the separated plasma to the patient and to the red blood cell flow path 10. Excess plasma generated by the separator is diverted along path 14 and subsequently combined downstream with RBC flow path 10, or alternatively exit the separator with the red blood cells in flow path 10. The amount of excess plasma that can alternatively flow from the separator with the red cells depends on the rates of Pump 30 and Pump 28. Pump 26 is preferably associated with flowpath 22 for delivering replacement fluid to the patient and pump 30 is preferably associated with flowpath 4 for withdrawing whole blood from the patient. Other types of flow controlling devices may also be used as controllers, including but not limited to valves and gravity-controlled flow controllers.

In FIG. 1, such controller 24 may include a main controller, generally indicated at 36, such as a programmable controller employing a programmable microprocessor, that is operatively associated with pumps 26, 28, and 30, and valves 32 and 34, to control the fluid flow through each of the associated pathways. In accordance with the present disclosure, the controller is programmed or configured to operate the system to achieve a target FCR, hematocrit, and change in patient fluid volume in a therapeutic red blood cell exchange procedure, and to optionally perform such a procedure with isovolemic hemodilution, as set forth in greater detail below.

Figure 2:
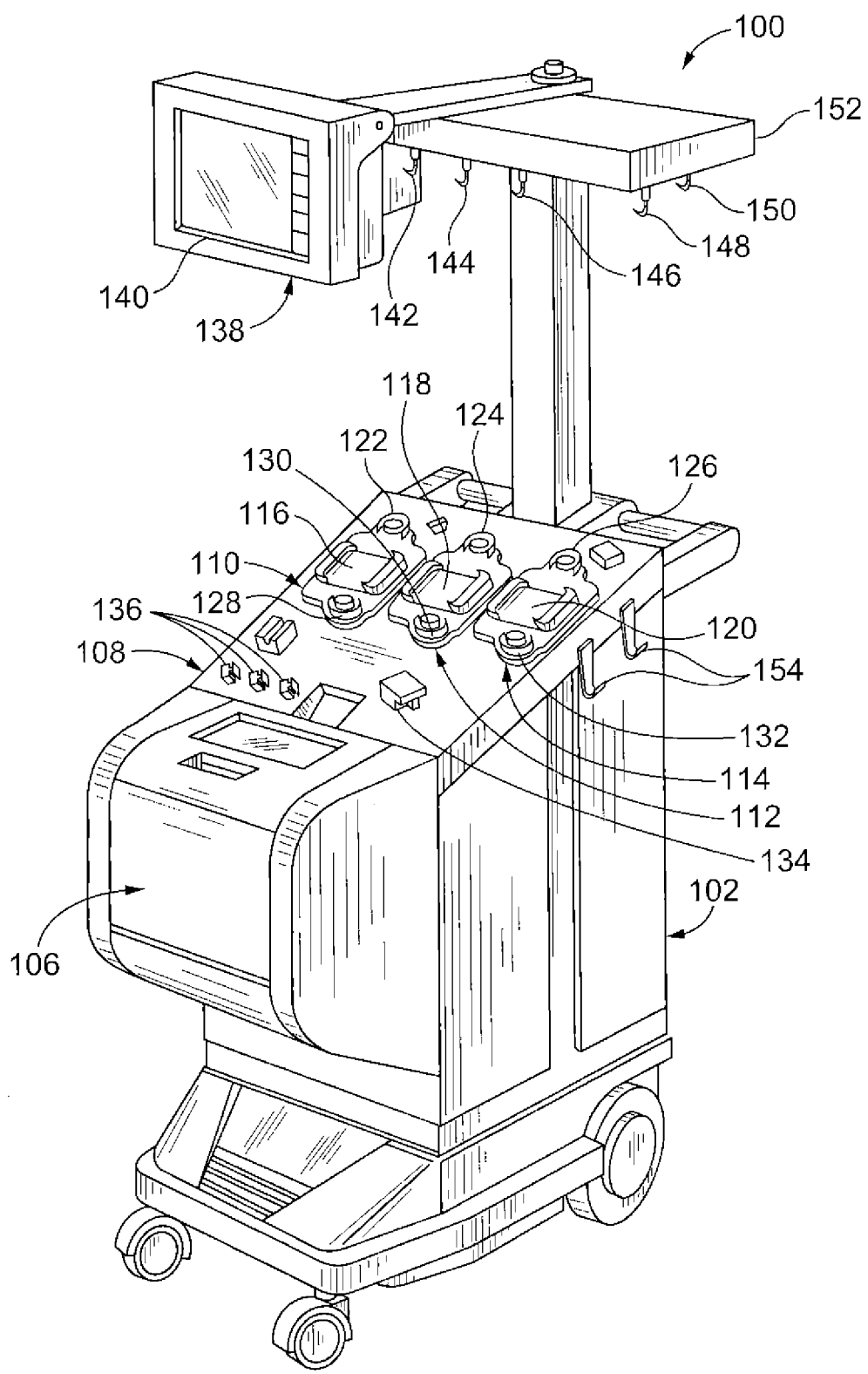
FIG. 2 is a perspective view of a reusable blood processing device that may be employed as part of or in association with the subject matter described.

FIG. 2 illustrates a centrifugal processing device, generally indicated at 100, that may be used for processing various fluids in accordance with the method and systems described herein. The illustrated embodiment is substantially identical to a commercial centrifuge sold by Fenwal, Inc. as the Amicus® separator, which is disclosed in numerous patents and patent applications, not limited to but including U.S. Pat. No. 5,868,696, to Giesler et al., issued Feb. 9, 1999, which is incorporated herein by reference.

As shown in FIG. 2, the centrifugal processing device 100 includes a separation assembly, specifically a centrifuge rotor assembly, generally within the housing indicated at 102, and is configured to control fluid flow through a disposable fluid processing set, (generally indicated 104 in FIG. 3), used in association with the processing device 100. As noted above, the separation assembly need not be a centrifugal processing assembly, and other separation technology or devices, such as membrane separators, may also be used. The separation assembly 102 receives and separates a biological fluid, such as whole blood and/or other biological fluids, into two or more constituent components. The separation assembly 102 is preferably adapted to be durable and reusable over a long term. The fluid processing set 104, in contrast, is disposable, and a fresh sterile set is assembled with the separation assembly 102 for each use.

In FIG. 2, the separation assembly 102 includes an access compartment, generally indicated at 106, which houses a portion of the disposable set 104, such that when the separation assembly 102 is activated, the constituent components are separated within such portion of the set 104. A panel, generally indicated at 108, provides a surface for receiving another portion of the disposable set 104. For example, the panel 108 includes three pumping and valving stations, or respective left, middle and right stations, generally indicated at 110, 112 and 114, in FIG. 2. Each station 110, 112 and 114 respectively includes a valve interface portion 116, 118 and 120, that controls the opening and closing of associated valves in a disposable flow control cassette, described further below. Each station also has a respective upper flow controlling device or pump 122, 124, 126 and a lower flow controlling device or pump 128, 130, 132. Each illustrated pump 122, 124, 126, 128, 130, 132 is a peristaltic pump adapted to be associated with a section of tubing to provide flow control, although other types of pumps or other flow controlling devices, such as diaphragm pumps or gravity controlled devices are also possible. The panel 108 may further include a detector 134, such as an optical detector, and/or other sensors or clamps, generally indicated at 136, for controlling and/or monitoring fluid and/or air flow in the disposable set 102.

As shown in FIG. 2, the system 100 further includes a controller, generally indicated at 138. The controller 138 may be a programmable controller that is operable to control the system 100 for various processes, including the therapeutic red blood cell exchange procedure described in greater detail below. An operator interface module 140 may allow for viewing of the past, current and/or upcoming operations and/or provide for operator input by way of a touch screen and/or one or more tactile controls. One or more weight scales 142, 144, 146, 148, 150 may be associated with the controller 138. Such scales may be attached to a platform or stand 152 that allows one or more fluid containers to be attached to or hung from the scales and to allow for weight measurement of such containers during and/or after the processing procedure. One or more hooks 154 may also extend downwardly from a right or left side of the panel 108 to allow attachment of other fluid containers and may also be associated with a weight scale, if desired.

Figure 3:
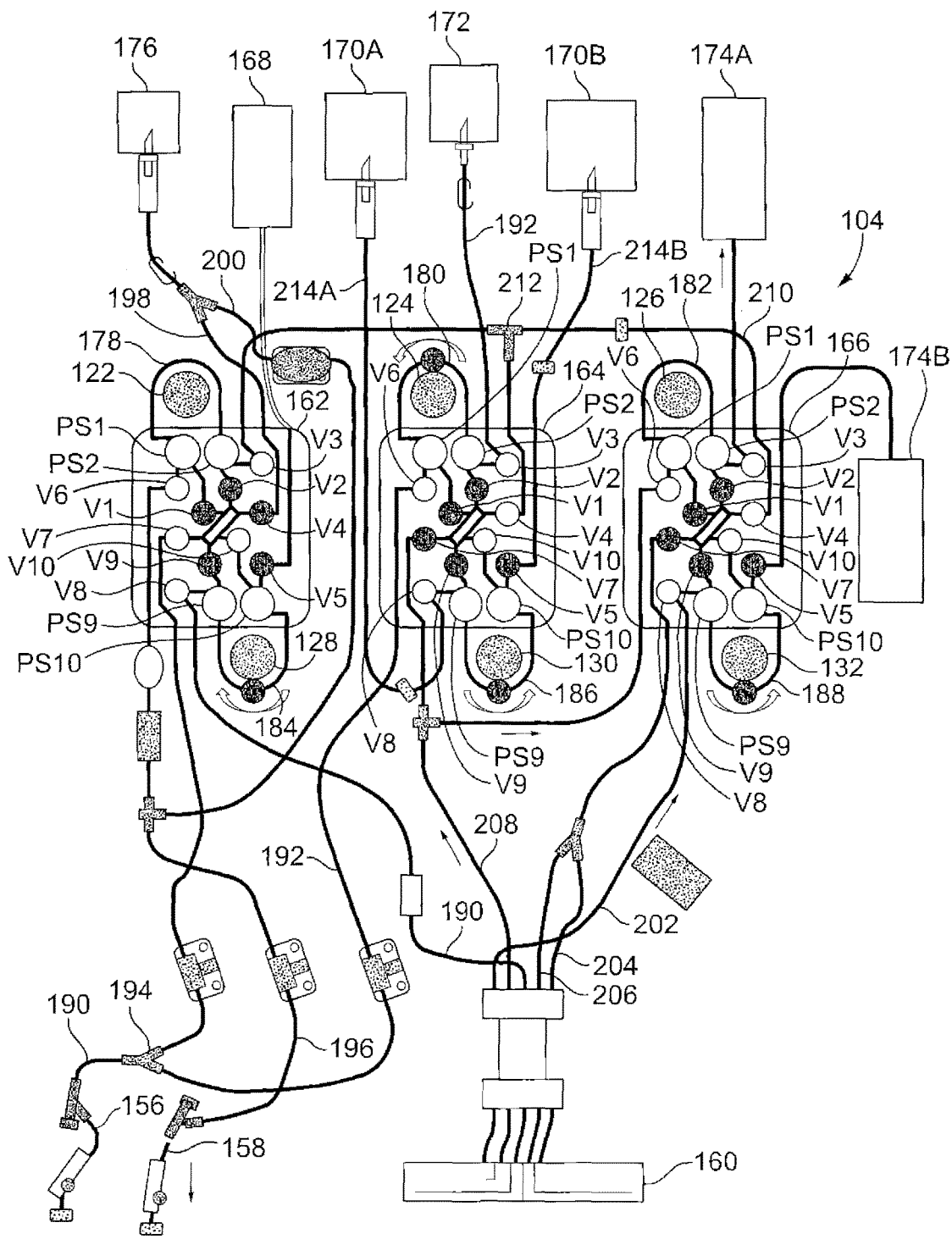
FIGS. 3 and 4 are plan views of a disposable tubing flow set for use with the processing device shown in FIG. 2, illustrating different modes of operation during a therapeutic red blood cell exchange procedure.
Figure 4:
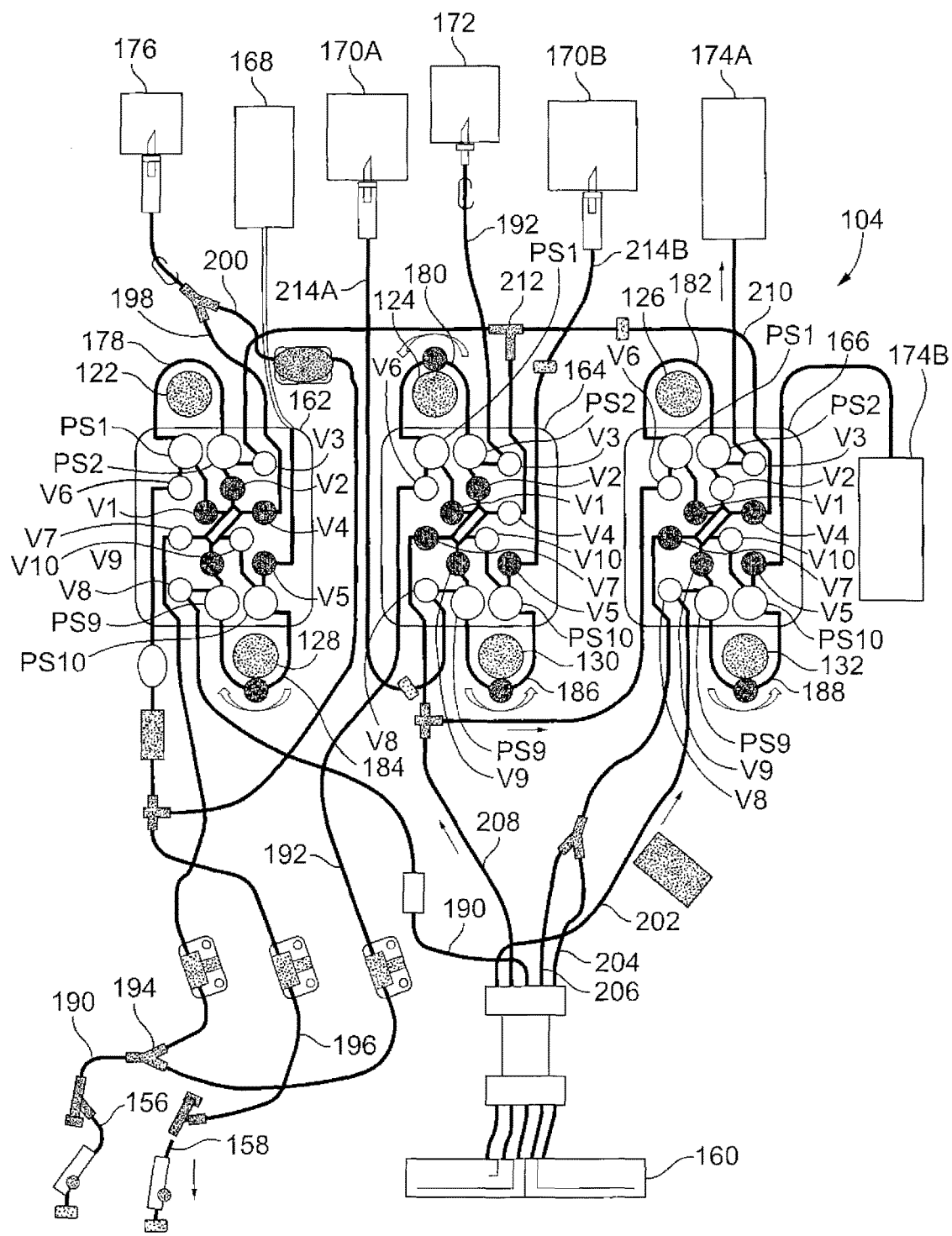

FIGS. 3 and 4 illustrate one possible disposable fluid flow processing set 104 that may be employed for use with the separation device for performing a therapeutic red blood cell exchange procedure in accordance with the present disclosure. FIG. 3 illustrates a fluid flow path in which the waste red cells exit the separator through 208, passes through the right cassette 166 and up to the waste container 174A. The plasma pump 132 sends the patient's plasma through path 210 and joins with replacement fluid at the connector indicated as 212. FIG. 4 illustrates an alternative pathway in which the plasma pump 132 sends the patient's plasma to the waste container 174A. This flowpath would only be necessary in the event that excess plasma is pumped from the separator and does not need to be returned to the patient. In the present disclosure, any reference to the plasma flow rate, $Q_P$, assumes that the fluid path being used is similar to the flow path illustrated by FIG. 3.

The disposable set 104 is preferably adapted to be loaded onto a separation assembly, such as shown and disclosed in U.S. Pat. No. 5,868,696, incorporated by reference above, although other separation assemblies are also possible. The set 104 includes a double needle (one for withdrawal of fluid from a patient and one for return of fluid to the patient) processing assembly, although it is understood that the present disclosure is not limited to double needle processing and may include single needle and other types of processing sets.

The set 104 includes a draw tubing 156 and a return tubing 158 (each having a patient access device such as a needle associated therewith), a processing chamber 160, left, middle and right pumping, flow control and valving cassettes 162, 164, 166, an auxiliary reservoir or container 168 for pressure relief or for diverted air, containers 170A, 170B for replacement fluids (such as saline, albumin and/or replacement red blood cells), a container 172 for an anticoagulant, containers 174A and 174B for red blood cell waste, and a container 176 for saline. Each container 170A, 170B, 174A, 172 and 176 may be respectively associated with a corresponding weight scale (see, e.g., weight scales 142, 144, 146, 148, 150 shown in FIG. 2) for determining the amount of fluid that is removed from or added to such container. The set 104 also includes various tubing paths discussed in further detail below.

Each cassette 162, 164 and 166 has a similar internal construction and, as such, only one cassette 162 will be described. However, it is understood that like alpha-numeric reference characters are applicable for each cassette. The left cassette 162 includes at least one and preferably a plurality of pressure sensing chambers, such as PS1, PS2, PS9, and PS10, preformed fluid flow pathways and at least one and preferably a plurality of valves, such as V1, V2, V3, V4, V5, V6, V7, V8, V9, and V10. In the modes of operation illustrated in FIGS. 3 and 4, a valve is "closed" if the circle indicating the valve is filled in and is "open" if the circle is not filled in. The number and configuration of such chambers and valves are not limited to that shown, and other variations are also possible, including variations for the interconnecting flow paths between such chambers and valves. Each of the chambers and valves preferably is associated with a respective portion of the respective pumping and valving station 110, 112 and 114 to control the flow of fluid.

As described above, each pump 122, 124, 126, 128, 130 and 132 may be a peristaltic pump adapted to be associated with a section of tubing to provide flow control. For example, each pump 122, 124, 126, 128, 130, and 132 may be associated with a respective tubing segment 178, 180, 182, 184, 186 and 188. The upper pumps 122, 124 and 126 are each associated with two pressure sensing chambers PS1 and PS2 with one being located downstream and the other located upstream of the pumps, depending on which direction is the desired flow direction, which direction may change, if desired, one or more times during and/or after the procedure. Similarly, the lower pumps 128, 130 and 132 are each associated with two pressure sensing chambers PS9 and PS10 located on either upstream or downstream side thereof. Such peristaltic pumps 122, 124, 126, 128, 130 and 132 are typically operated by rotation and include one or more outward extensions, roller or the like that act on the exterior of the respective tubing segment 178, 180, 182, 184, 186 and 188 to progressively compress or "push" fluid in the desired direction of flow. The pumps are bi-directional, and in the modes of operation illustrated in FIGS. 3 and 4, the direction of rotation of the pumps, and consequently the direction of fluid flow, is indicated by an arrow.

The set 104 further includes a first flow path 190 that fluidly communicates with the draw tubing 156 for withdrawing whole blood from a patient. An anticoagulant flow path 192 may communicate with the first flow path 190 at a Y-branch connector 194 to allow anticoagulant to mix with the withdrawn whole blood. Anticoagulant from the anticoagulant container 172 may be pumped to the first flow path 190 by the upper or anticoagulant pump 124 of the middle cassette 164 and flow through open valves V3 and V6 of such cassette to mix with the withdrawn whole blood. The set 104 includes a return or replacement fluid flow path 196 that fluidly communicates with the return tubing 158 to allow one or more fluids, such as a replacement fluid, to flow to the patient. One or more saline flow paths 198 and 200 may also be in respective communication with the whole blood and return flow paths 190 and 196 to allow saline flow, if desired, before, during and/or after the procedure.

By way of example and not limitation, the withdrawn whole blood flows into the first flow path 190 and through the left cassette 162 and the lower or whole blood pump 128 of such cassette. The first flow path 190 preferably communicates with the processing chamber 160 so as to allow the withdrawn whole blood from the patient to be separated into selected constituent blood components, such as red blood cells, platelets and/or plasma.

Outlet flow paths 202 and 208 may allow separated blood components, such as red blood cells, plasma and/or platelets, to separately exit the processing chamber 160. For example, separated red blood cells from the processing chamber 160 may flow through a red blood cell path 208. Separated plasma from the processing chamber 160 may flow through the plasma flow path 202. An optical detector, such as the optical detector 134 discussed above, may be associated with the plasma flow path 202 to assist in optical detection of blood components, e.g. platelets or red cells, in the plasma constituent.

Separated red blood cells flowing from the processing chamber 160 preferably flow through the red blood cell flow path 208 to one of the red blood cell containers 174A or 174B. Separated red blood cells may flow through the right cassette 166 into one of the containers 174A or 174B. Separated plasma preferably is pumped by operation of the lower pump 132 of the right cassette 166. As discussed above, the removed red blood cell containers 174A, 174B may also be associated with weight scales for measuring the amount of the separated red blood cells flowing into such containers during the procedure.

The separated plasma from the processing chamber 160 flows through the plasma flow path 202 either to one of the containers 174A, 174B, or is returned to the patient. For example, the separated plasma may flow from the processing chamber 160 through the right cassette 166 to a first passageway 210 in communication with the return flow path 196. Separated plasma is preferably pumped by the lower or plasma pump 132. Separated plasma may flow into the return flow path 196 at a selected location or connector 212, which combines the plasma and replacement fluid into a combined fluid stream for return to the patient.

Replacement fluid flows from one of the replacement fluid containers 170A, 170B to the patient through the return flow path 196. For example, the replacement fluid flows from either container 170A or 170B through a replacement fluid source path 214A or 214B to the middle cassette 164. The lower or replacement pump 130 may assist the flow of the replacement fluid. The replacement fluid flows into the return flow path 196 and flows to the patient. As noted above, separated plasma may be combined with the replacement fluid in a single fluid stream. The return flow path 196 may also flow through the left cassette 162. A combined fluid stream may also be pumped by operation of the upper left or return pump 122 to assist the return flow to the patient.

Performance of the Method

A method of performing a red blood cell exchange procedure to achieve a target end hematocrit and fluid balance may comprise the steps of determining the patient total blood volume; determining the total amount of red blood cells to be removed from the patient; determining the total replacement fluid volume needed; determining a target volume of whole blood to be processed; processing a volume of whole blood; determining the processing time remaining; determining the amount of replacement fluid remaining; determining the replacement fluid flow rate; determining an amount of plasma to be returned to the patient; determining a plasma flow rate for returning plasma to the patient; determining a flow rate for plasma to be sent to a waste receptacle; and determining a return rate as limited by citrate infusion to the patient.

The amount of red blood cells to be removed from the patient may be calculated as the product of the red blood cell exchange volume and a total red blood cell volume for the patient based on the calculated volume of whole blood and the starting hematocrit of the patient. Alternatively, the amount of RBCs to be removed may be calculated by entering a fraction of cells remaining and calculating an exchange volume percent multiplied by the total red blood cell volume of the patient and dividing by 100.

The amount of red blood cells to be removed from the patient during the exchange procedure may be specified by an operator. In addition, the amount of fluid replacement volume needed to perform the procedure may be calculated by assuming that the amount of red blood cells to be replaced equals the amount that was calculated to be removed in order to maintain the same level of total red blood cell volume, and adjusting the volume depending on whether the target end hematocrit is greater, less, or equal to the starting hematocrit of the patient. Also, the replacement volume needed may be adjusted by comparing the average hematocrit of the replacement fluid to the target end hematocrit of the patient, and the volume of whole blood to be processed may be based on the calculated total amount of red blood cells to be removed and the starting hematocrit of the patient.

Figure 7:
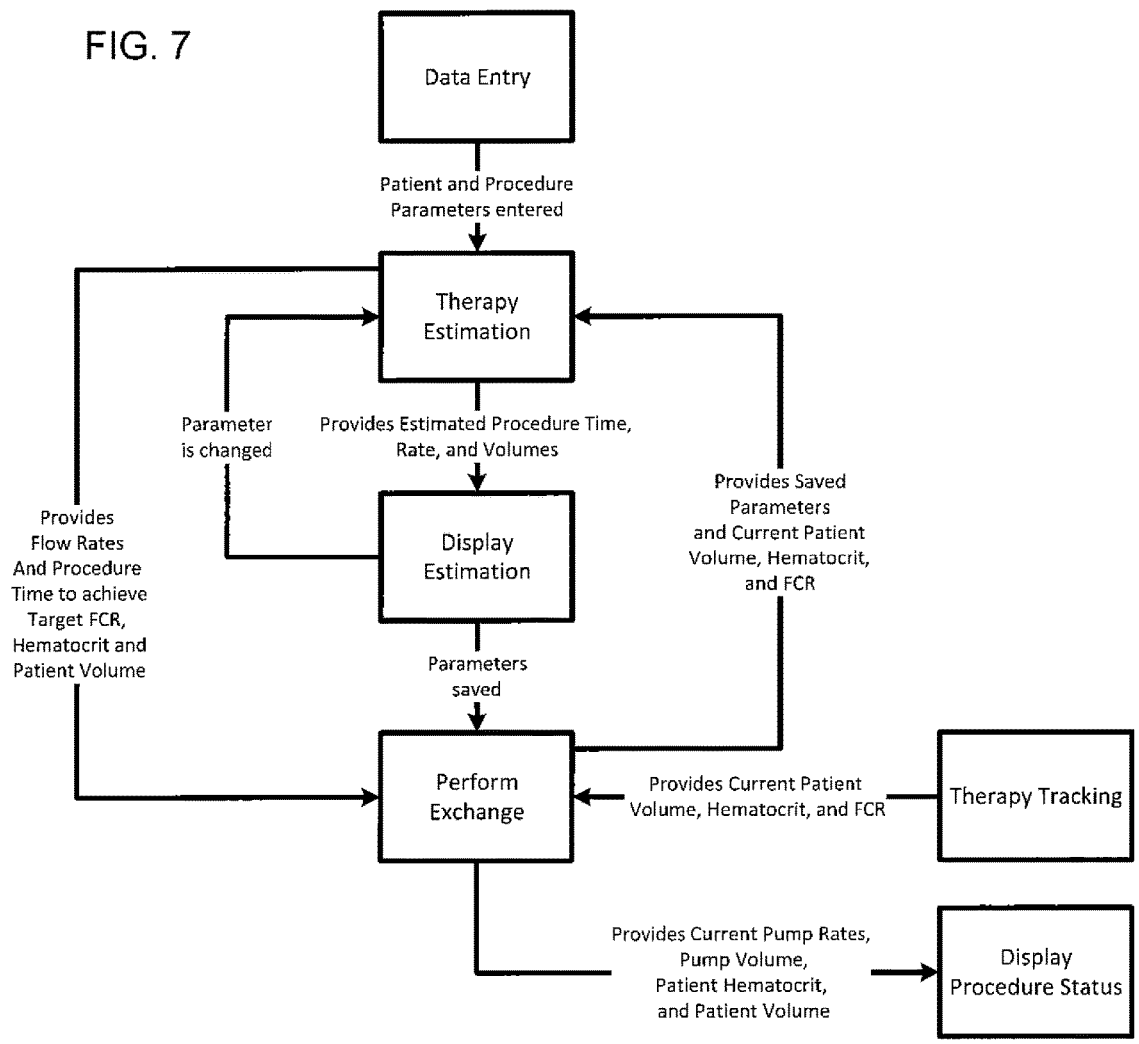
FIG. 7 is a flow chart setting forth a method for achieving a target end hematocrit, fraction of cells remaining, and patient volume during a therapeutic red blood cell exchange procedure in accordance with the present disclosure.

The various steps of the method are contemplated in the flow chart attached as FIG. 7. It should be understood that the flow chart is comprehensive, and that one or more of the steps may be modified or omitted, according to the requirements of the operator and patient.

The method as illustrated by FIG. 7 comprises several stages, including the entry of certain required data, the performance of calculations in order to establish the procedure parameters, initialization and performance of the procedure to completion in accordance with the procedure parameters.

In broad terms, in accordance with the method disclosed herein, patient height, weight, gender, hematocrit, target FCR, replacement fluid hematocrit, target end hematocrit, and target change in patient fluid volume are inputted to the system controller. The controller then calculates outputs of the whole blood, replacement fluid, and plasma flow rates required to simultaneously achieve the inputted clinical targets. The system will display the estimated replacement fluid volume required, the estimated procedure time, and estimated anticoagulant needed, and allow the user to make changes to the inputs to meet the needs of the patient. Alternatively, a target replacement fluid volume may be inputted and the target FCR will be calculated and outputted.

Data Entry Stage

Turning first to the data entry stage, patient data and targets must be entered so that the necessary calculations can be performed to estimate the volume of replacement fluid necessary, the procedure time, the volume of anticoagulant returned to the patient, and the volume of anticoagulant required. The system is configured so that it will not allow the operator to progress forward until the appropriate data have been entered. The process defines the triggers to alert the operator if additional waste replacement fluid containers are necessary, if the entered blood-to-anticoagulant ratio, ACR, is unattainable, or if adjustments to target FCR, end hematocrit or fluid balance are necessary.

Turning to FIG. 7, the data entry process is initiated by first determining the required patient data, including gender, height, and weight, entering that information so that the patient's initial total blood volume, $V_0$, may be calculated. This is done using, e.g., the generally accepted equations developed by Nadler et al. Alternatively, the total blood volume may be entered by the operator, which may be preferred for small patients, such as children, as the Nadler equations lose accuracy for patients weighing less than 55 lbs (25 kg).

The patient's initial and target final hematocrits, $H_{T0}$ and $H_{TF}$ respectively, are then entered as is the target change in patient fluid volume, $\Delta V$. This may be entered directly or as a percentage of the initial patient fluid volume, $V_0$.

Next, the information for determination of the FCR is entered. This may be accomplished in two ways. The operator may enter either the FCR directly or the volume of autologous RBCs to be removed, $V_{RBCR}$. If the latter quantity is entered, then the system calculates the FCR as $$FCR = \frac{V_{RBCR}}{H_{T0}V_0}. \tag{1}$$

Then, the system preferably establishes the procedure parameters in as set forth in detail below.

Parameter Calculation Stage

In keeping with a further aspect of the disclosure, the controller is programmed to derive various parameters for an RBC exchange procedure in which, for example, normal red blood cells are transfused into a patient with sickle-cell anemia while sickle cells are simultaneously removed, thus performing the Therapy Estimation function of FIG. 7.

Figure 5:
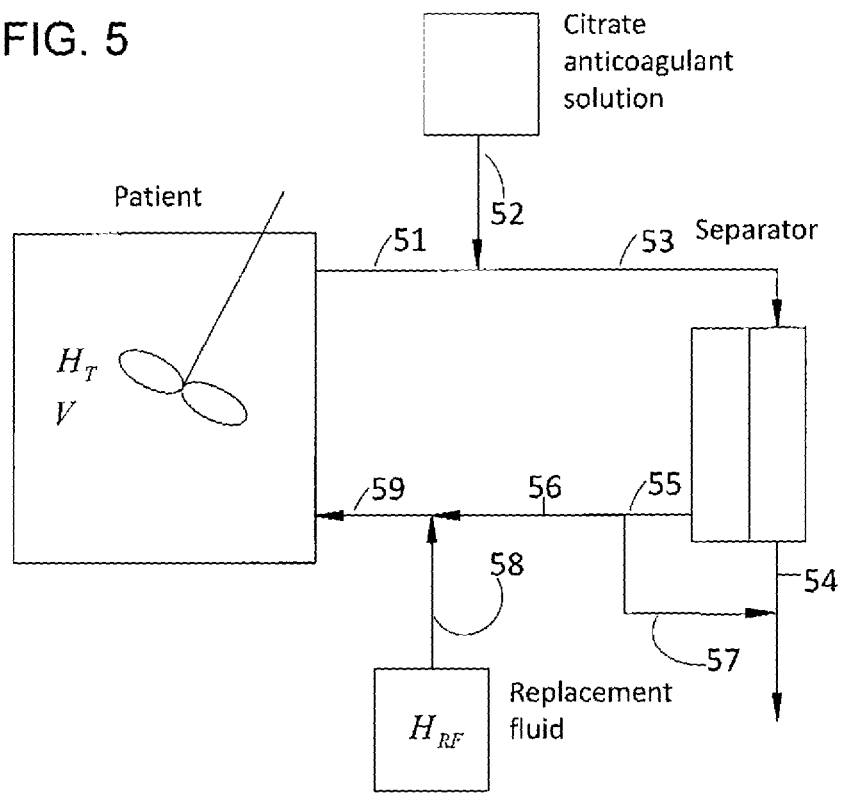
FIG. 5 is a schematic representation of a model for a red blood cell exchange procedure by which certain operating parameters may be determined.

With reference to FIG. 5, a schematic representation of an RBC exchange procedure is seen in which blood at a hematocrit $H_T$ is withdrawn through flowpath 51 at a flow rate $Q_{WB}$ from a patient who is modeled as a well-stirred tank having an initial volume $V_0$ and initial total cell hematocrit of $H_{T0}$. Sodium citrate anticoagulant solution (AC) having a sodium citrate concentration $C_{AC}$ flows through flowpath 52 at a flow rate $Q_{AC}$ and combines with flowpath 51 to form flowpath 53 which leads to the separation device. Blood enters the separator where it is separated into concentrated cells which exits the device through flowpath 54 at a flow rate $Q_4$ and plasma which exits the device through flowpath 55. A portion of this plasma is returned to the patient through flowpath 56 at a flow rate $Q_P$ and the remainder is combined with the concentrated cell in flowpath 54 through flowpath 57 or may exit the separator with the red cells through flowpath 54. The replacement fluid (normal blood) at a hematocrit of $H_{RF}$ and a flow rate $Q_{RF}$ in flowpath 58 combines with the plasma in flowpath 56 and the combined fluid is returned to the patient through flowpath 59. By reference to this model, algorithms for determining various operating parameters for the RBC exchange procedure may be derived, as set forth in detail below. Specifically, these parameters are the flow rates $Q_{WB}$, $Q_P$, and $Q_{RF}$.

First the donor draw blood flow rate, $Q_{WB}$, is set to some maximum value, for example 120 mL/min. As detailed below, this value is later adjusted if necessary after determination of corresponding values of $Q_P$ and $Q_{RF}$ if the resulting citrate infusion rate CIR is greater than some upper limit, $CIR_{MAX}$.

Of interest are the patient FCR, hematocrit $H_T$, and blood volume, V, all as functions of time. First, the time required to achieve a certain final hematocrit $H_{TF}$ based on the total cell volume fraction is determined. To this end, the mass balance on all cells requires that $$\frac{d(VC_T)}{dt} = \dot{m}_{T9} - \dot{m}_{T1} \tag{2}$$

where $\dot{m}_{T1}$ and $\dot{m}_{T9}$ are the mass flow rates of red blood cells though flowpaths 51 and 59, respectively, $C_T$ is the mass concentration of cells, and t is time. Flowpath 56 contributes no cells. Thus $$\dot{m}_{T9} = \dot{m}_{T8}. \tag{3}$$

and $$\frac{d(VC_T)}{dt} = \dot{m}_{T8} - \dot{m}_{T1}. \tag{4}$$

Since the density of the cells is approximately constant, this can be written in terms of hematocrit as $$\frac{d(VH_T)}{dt} = H_{RF}Q_{RF} - H_{T1}Q_{WB}. \tag{5}$$

Further, since the "tank" (i.e., the patient) is well-stirred, $$H_{T1} = H_T \text{ and } \frac{d(VH_T)}{dt} = H_{RF}Q_{RF} - H_TQ_{WB}. \tag{6}$$

Expanding the time derivative, gives $$V\frac{dH_T}{dt} + H_T\frac{dV}{dt} = H_{RF}Q_{RF} - H_TQ_{WB}. \tag{7}$$

Since the flow rates are constant, $$\frac{dV}{dt} = Q_{RF} + Q_P - Q_{WB} \tag{8}$$

and:

$$V = V_0 + (Q_{RF} + Q_P - Q_{WB})t. \tag{9}$$

Combining Equations 7 through 9 and rearranging yields:

$$\frac{dH_T}{dt} = \frac{Q_{RF}H_{RF} - (Q_{RF} + Q_P)H_T}{V_0 + (Q_{RF} + Q_P - Q_{WB})t}. \tag{10}$$

Separation of variables, integration, and application of the initial condition that $H_{T(0)} = H_{T0}$ yields $$H_T = \frac{H_{RF}}{F} - \left[\frac{H_{RF}}{F} - H_{T0}\right]\left[\frac{V_0}{V_0 + (Q_{RF'} + Q_P - Q_{WB})t}\right]^M \quad Q_{RF} + Q_P \neq Q_{WB} \tag{11a}$$

-continued $$H_T = \frac{H_{RF}}{F} - \left[\frac{H_{RF}}{F} - H_{T0}\right]\left[\exp\left(\frac{-(Q_{RF'} + Q_P)t}{V_0}\right)\right] \quad Q_{RF} + Q_P = Q_{WB}. \quad (11b)$$

where $$F = (Q_{RF} + Q_P)/Q_{RF} \quad (12)$$

and $$M = \frac{Q_{RF} + Q_P}{Q_{RF} + Q_P - Q_{WB}} \quad (13)$$

Solving Equations 11a and 11b for the time required to achieve a certain final hematocrit, $H_{TF}$, yields:

$$t_{HF} = \frac{V_0}{(Q_{RF} + Q_P - Q_{WB})}\left[\frac{1}{Z^{1/M}} - 1\right] \quad Q_{RF} + Q_P \neq Q_{WB} \quad (14a)$$

$$t_{HF} = \frac{-V_0}{(Q_{RF} + Q_P)}[\ln Z] \quad Q_{RF} + Q_P = Q_{WB} \quad (14b)$$

where:

$$Z = \frac{H_{T1} - FH_{TF}}{H_{T1} - FH_{T0}}. \quad (15)$$

Then the hematocrit with respect to remaining patient cells is considered. Mass balance on original patient cells requires that $$\frac{d(VC_P)}{dt} = -\dot{m}_{WB,P}. \quad (16)$$

where $C_P$ is the concentration of patient cells and $\dot{m}_{P3}$ is the mass flow rate of original patient cells out of the patient.

Following the same analysis as above for the total cells, this becomes $$\frac{dH_P}{dt} = \frac{-(Q_{RF} + Q_P)H_P}{V_0 + (Q_{RF} + Q_P - Q_{WB})t}. \quad (17)$$

Given the initial condition that $H_P = H_{T0}$, the patient's initial hematocrit, this has the solution $$\frac{H_P}{H_{T0}} = \left[\frac{V_0}{V_0 + (Q_{RF} + Q_P - Q_{WB})t}\right]^M \quad Q_{RF} + Q_P \neq Q_{WB} \quad (18a)$$

$$\frac{H_P}{H_{T0}} = \exp\left[-\frac{Q_{WB}}{V_0}t\right] \quad Q_{RF} + Q_P = Q_{WB}. \quad (18b)$$

Then, the fraction of patient cells remaining, FCR, relative to the initial number of patient cells is defined by $$FCR = \frac{V_{PF}}{V_{P0}} \quad (19)$$

where $V_{P0}$ and $V_{PF}$ are the volumes of autologous cells at the beginning and end of the procedure, respectively.

Correspondingly, the running value of FCR during the course of the procedure is:

$$FCR = \frac{V_{CP}(t)}{V_{CP0}}. \quad (20)$$

In terms of hematocrits, H, this is:

$$FCR = \frac{H_P V}{H_{T0} V_0}. \quad (21)$$

This is Equation 18 scaled by the (possibly changing) relative blood volume. In the special case of a fixed patient blood volume, the scaling factor is unity and $$FCR = \frac{H_P}{H_{T0}}. \quad (22)$$

Substituting Equation 18 into Equation 21 gives $$FCR = \left[\frac{V_0}{V_0 + (Q_{RF} + Q_P - Q_{WB})t}\right]^{(M-1)} \quad Q_{RF} + Q_P \neq Q_{WB} \quad (23a)$$

$$FCR = \exp\left(-\frac{Q_{WB}}{V_0}t\right) \quad Q_{RF} + Q_P = Q_{WB} \quad (23b)$$

It should be noted that clinically in the case of sickle cell anemia, FCR may be determined by measuring HgS, the fraction of the total hemoglobin which is in the S form:

$$HgS = \frac{Hgb_S}{Hgb_T} \quad (24)$$

where $Hgb_S$ and $Hgb_T$ are, respectively, the S-form and total hemoglobin concentration in the blood. Thus:

$$FCR_C = \frac{HgS(t)}{HgS_0} \quad (25)$$

In terms of hematocrit, Equation 24 is:

$$HgS = \frac{H_S}{H_T}. \quad (26)$$

Thus:

$$FCR_C = \frac{H_{T0}}{H_T}\frac{H_S}{H_{S0}}. \quad (27)$$

But since the volume fractions of sickled and normal cells decay at the same rate, $$\frac{H_S}{H_{S0}} = \frac{H_T}{H_{T0}} \quad (28)$$

and thus $$\frac{FCR}{FCR_C} = \frac{V}{V_0}\frac{H_T}{H_{T0}}. \quad (29)$$

For the special case of no volume or hematocrit change, $FCR=FCR_C$.

Solving Equation 23 for the processing time, $t_{FCR}$, required to achieve a specified value of FCR yields $$t_{FCR} = \frac{V_0}{(Q_{RF} + Q_P - Q_{WB})}\left[\frac{1}{FCR^{\frac{1}{M-1}}} - 1\right] \quad Q_{RF} + Q_P \neq Q_{WB} \quad (30a)$$

$$t_{FCR} = \frac{-V_0}{Q_{WB}}[\ln FCR] \quad Q_{RF} + Q_P = Q_{WB} \quad (30b)$$

Thus, the clinical objectives may be simultaneously achieved as follows:

Equations 14 and 30 define the procedure times, $t_{HF}$ and $t_{FCR}$ required to achieve the clinically targeted values of $H_{TF}$ and FCR, respectively. Correspondingly, the time required to achieve the prescribed volume change, $\Delta V$, is $$t_V = \frac{\Delta V}{Q_1 + Q_5 - Q_3}. \quad (31)$$

Simultaneous achievement of these objectives requires that $$t_{FCR} = t_{HF} = t_V. \quad (32)$$

Equating first Equations 30 and 31 gives $$\frac{\Delta V}{V_0} = \left[\frac{1}{FCR^{\frac{1}{M-1}}} - 1\right]. \quad (33)$$

Solving for the parameter M yields $$M = 1 - \frac{\ln(FCR)}{\ln(1 + \Delta V/V_0)} \quad (34)$$

Equating now Equations 14 and 31 gives $$\left(\frac{H_{TS} - FH_{TF}}{H_{TS} - FH_{T0}}\right)^{1/M} = FCR^{\frac{1}{M-1}} \quad (35)$$

From this the parameter F is calculated as follows:

$$F = \frac{H_{RF}}{H_{T0}}\left[\frac{FCR^{\frac{M}{M-1}} - 1}{FCR^{\frac{M}{M-1}} - \frac{H_{TF}}{H_{T0}}}\right] \quad Q_{RF} + Q_P \neq Q_{WB} \quad (36)$$

$$F = \frac{H_{RF}}{H_{T0}} \quad Q_{RF} + Q_P = Q_{WB} \quad (37)$$

Given $Q_{WB}$, M, and F, the replacement fluid flow rate $Q_{RF}$ required is then calculated using $$Q_{RF} = \frac{M}{F(M-1)}Q_{WB}. \quad (38)$$

Finally, the required plasma flow rate $Q_P$ is then determined by $$Q_P = (F-1)Q_{RF}. \quad (39)$$

Thus from Equations 38 and 39, $$\frac{Q_{RF}}{Q_{WB}} = \frac{M}{F(M-1)}. \quad (40)$$

and $$\frac{Q_P}{Q_{WB}} = \frac{M(F-1)}{F(M-1)}. \quad (41)$$

Next, the controller checks whether the citrate infusion rate expected from the calculated values whole blood, replacement fluid, and plasma flow rates is above $CIR_{MAX}$. To do this, the maximum patient hematocrit, $H_{MAX}$, is first selected:

$$H_{MAX} = \max(H_{T0}, H_{TF}). \quad (42)$$

This is then used to calculate the volume fraction of sodium citrate solution in the plasma, $\phi AC$ using $$\phi_{AC} = \frac{1}{(1 - H_{MAX})ACR + 1}. \quad (43)$$

where ACR is the whole blood to anticoagulant solution volume ratio defined by $$ACR = \frac{Q_{WB}}{Q_{AC}}. \quad (44)$$

The expected CIR is then given by $$CIR = Q_{RP}C_{RP} + \phi_{AC}Q_P C_{AC}. \quad (45)$$

where C is sodium citrate concentration, for example in mg/mL, and the subscripts RP and AC refer respectively to replacement fluid and anticoagulant solution. An adjustment factor, K, is then calculated as $$K = \frac{CIR_{MAX}}{CIR} \quad CIR > CIR_{MAX} \quad (46)$$

$$K = 1 \quad CIR <= CIR_{MAX}. \quad (47)$$

This adjustment factor is then used to scale down all the previously calculated flow rates. Thus, $$Q_{WB,K} = KQ_{WB} \quad (48)$$

$$Q_{AC,K} = KQ_{AC} \quad (49)$$

$$Q_{RP,K} = KQ_{RP} \quad (50)$$

$$Q_{P,K} = KQ_P. \quad (51)$$

Initialization and Performance of Procedure to Completion

Once the controller calculates the pump rates and time necessary to achieve the procedure objectives as indicated by the Therapy Estimation function in FIG. 7, the estimates are displayed for the operator, as indicated by the Display Estimation function of FIG. 7. If the operator changes a data entry input, the Therapy Estimation function is re-executed. If the operator saves the data entry inputs and they are deemed achievable by the controller, the calculations of pump rates and time are applied to the exchange procedure.

As the procedure progresses, the Therapy Tracking function calculates the current patient volume, current patient hematocrit, and current patient fraction of cells remaining. This information can then be used by the Therapy Estimation function in the event re-calculation of the procedure parameters is needed. Events that can trigger a re-calculation are the changing of a data entry input, an interruption to the procedure that stops the pumps, or a mode change. The exchange process will also display current patient and procedure status such as current pump rates and volumes pumped, patient hematocrit and patient volume change. It may happen from time to time that the whole blood flow rate needs to be changed to accommodate various changes in the system, such as excess negative pressure in the draw line due to vein-access issues. In these cases, the controller simultaneously adjusts the replacement fluid, plasma, and anticoagulant solution accordingly. Note however that the parameters M and F, as defined above, depend only on the initial patient conditions and the target procedure outcomes. The controller may also be configured to adjust these values if a change in target values is required during the procedure.

EXAMPLE

As noted above, the algorithms derived above are preferably programmed into the microprocessor of the main controller for the separation device. The following is an example of RBC exchange procedures in which the operating parameters are determined by the foregoing algorithms and are set forth below.

| RBC Exchange Example | | |
|---|---|---|
| Parameter, units | Symbol | Value |
| Patient initial fractional hematocrit | $H_{T0}$ | 0.35 |
| Patient initial hemoglobin S fraction | $HgS_0$ | 0.80 |
| Replacement blood fractional hematocrit | $H_{RF}$ | 0.60 |
| Draw flow rate, ml/min | $Q_{WB}$ | 70 |
| Patient initial blood volume, mL | $V_0$ | 5000 |
| Prescribed FCR | FCR | 0.30 |
| Prescribed $H_{TF}$ | $H_{TF}$ | 0.25 |
| Prescribed volume change, mL | $V_F$ | −200 |
| Parameter F | F | 2.933 |
| Parameter M | M | −28.493 |
| Plasma flow rate, mL/min | $Q_P$ | 44.572 |
| Replacement fluid flow rate, mL/min | $Q_{RF}$ | 23.055 |
| Processing time, min. | t | 84.27 |

Figure 6:
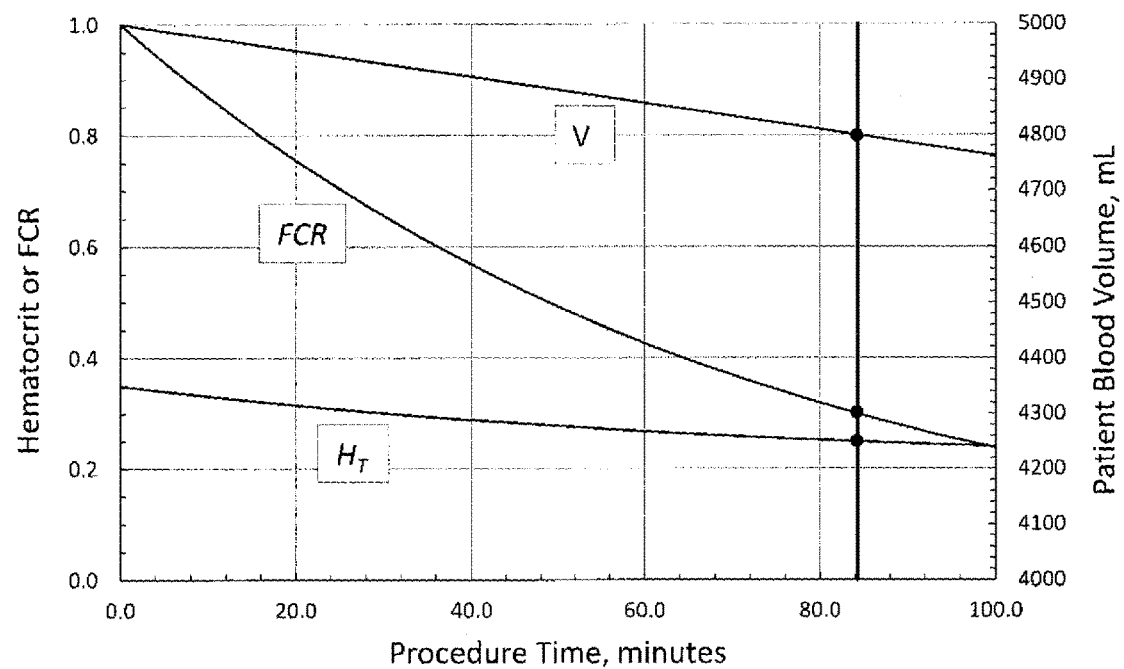
FIG. 6 is a graph illustrating the relationship between the hematocrit, the fraction of cells remaining, and the patient fluid volume vs. procedure time in a continuous RBC-exchange procedure in which the process objectives are met simultaneously.

The time course of this example procedure is illustrated in FIG. 6. It can be seen that, in accordance with the present disclosure, the three prescribed clinical targets of FCR, $H_{TF}$, and ΔV are all met simultaneously.

Performance of Exchange Procedure with Isovolemic Hemodilution

In accordance with a further aspect of the present disclosure, the operator may want to decrease the patient's hematocrit at the start of the red blood cell exchange procedure, with the intent of achieving a more efficient reduction of the patient's level of hemoglobin S (HbS) and more efficient utilization of the replacement red blood cells. The operator does this by using a predetermined volume of a cell-free replacement fluid as the replacement fluid for the first quantity of whole blood drawn, instead of replacement red blood cells. Thus, in accordance with this aspect of the disclosure, a method is provided in which patient plasma is initially returned with a cell-free replacement fluid, such as saline or albumin, while achieving the target dilution and patient isovolemia. In doing so, the operator may enter either a target dilution hematocrit or a target dilution volume of replacement fluid. The system automatically transitions into a normal red cell exchange process that uses red cells as the replacement fluid. Different ramping profiles may be used for the flow rate for the replacement red blood cells to reach the targeted end patient hematocrit.

This method increases the ease of use by allowing an operator to input a target dilution hematocrit and having the system calculate the necessary volumes to achieve that dilution and maintain patient isovolemia. Alternatively, a hematocrit sensor on the waste RBC line may be used to confirm the target dilution. Once the dilution is achieved, the system automatically transitions to the normal red cell exchange process that uses red cells as the replacement fluid. These methods provide the operator with more flexibility, as the system will 1) allow the operator to input a target dilution volume of replacement fluid, and 2) display the amount of replacement fluid used and allow the operator to switch to the secondary scale containing the red cell replacement fluid and change the replacement fluid type on the user interface. The operator can also program how the end patient hematocrit is achieved, either by gradually increasing the hematocrit in a linear manner up toward the target, or keeping the hematocrit at a low level for the majority of the procedure and having a steeper transition to the target end hematocrit at the end of the procedure.

If the operator chooses to perform isovolemic hemodilution, three options are provided for initiating the procedure. In a first option, the operator enters a Target Dilution Hematocrit in addition to the patient and procedure parameters required to perform the red blood cell exchange (as described above), and sets the replacement fluid type, which may be saline, albumin, or an albumin solution. Using the patient's initial hematocrit, the system calculates the amount of patient whole blood to process in order to achieve the Target Dilution Hematocrit. This calculation takes into account that non-cellular fluid is given to replace the amount of red blood cells removed. The system uses the plasma flow rate from the separation device to calculate the flow rate at which the replacement fluid pump should operate to maintain patient isovolemia. Once the calculated amount of whole blood is processed, the system transitions to a red blood cell exchange by switching to the red blood cell replacement fluid container, and using the calculations in the exchange process to control the pump rates.

In a second option, the operator's calculations are used to determine the target dilution hematocrit, and the operator then enters in a Target Dilution Volume. The replacement fluid type is set to either saline or albumin. The system processes the patient's whole blood, but does not return the patient's plasma. Once the target volume of dilution replacement fluid is used, the system transitions to red cell exchange by switching to the red blood cell replacement fluid container and using the calculations in the exchange process to control the pump rates.

In a third option, the operator's calculations to achieve the Target Dilution Hematocrit are used, and the operator sets the replacement fluid type to either saline or albumin. The system will process the patient's whole blood and will return the patient's plasma and the replacement fluid of saline or albumin. The operator is able to view the amount of replacement fluid returned from a user interface. Once the operator sees that the calculated replacement volume is reached, the operator switches to the red blood cell replacement fluid container and changes the replacement fluid type to red blood cells.

Before the end of the procedure, the patient's hematocrit must be increased to achieve the targeted end hematocrit. This is accomplished by returning red blood cells at a faster rate than they are removed. The way in which this end hematocrit is achieved may be programmed to follow a set profile. For example, the hematocrit may be increased gradually in a linear fashion to the end target. Alternatively, the diluted hematocrit may be maintained for a set portion of the procedure and then increased non-linearly to achieve the target by the end of the procedure.

The system may alternatively use a feedback loop to achieve the target dilution hematocrit. The system estimates the patient's hematocrit based on the whole blood flow rate, the plasma flow rate, and the estimated packed red cell hematocrit. Using the estimated patient hematocrit, the system continues to process whole blood until the target dilution hematocrit is achieved. Alternatively, real time patient hematocrit may be determined by a hematocrit sensor.

As can be seen from the above description, the present disclosure has several different aspects, which are not limited to the specific structures and methods shown in the attached drawings or described above. Variations of these concepts or structures may be embodied in other structures for carrying out other applications in the medical or other fields without departing from the scope of the disclosure.

What is claimed is:

1. A blood processing system comprising:
a blood separation device for separating whole blood into a red blood cell component and a plasma component;
an inlet flowpath including a pump operable at a prescribed flow rate $Q_{WB}$ to convey whole blood from a patient having a whole blood volume V, a whole blood hematocrit value $H_T$ into the separation device;
a return flowpath to convey fluid to the patient;
a first outlet flowpath including a pump operable at a prescribed flow rate $Q_P$ to convey separated plasma from the separation device;
a second outlet flowpath to convey separated red blood cells from the separation device;
a first source of replacement fluid comprising red blood cells having a hematocrit $H_{T1}$ in fluid communication with the return flowpath;
a third flowpath including a pump operable at a prescribed flow rate $Q_{RF}$ to convey replacement red blood cells to the patient; and
a controller programmed: to accept or derive input values for a target post-procedure fraction of patient cells remaining (FCR), hematocrit ($H_{TF}$), and patient fluid volume change ($\Delta V$); the initial patient fluid volume ($V_0$); the initial patient hematocrit ($H_{T0}$), the hematocrit of the replacement fluid ($H_{T1}$) in the first source; and the maximum blood draw rate ($Q_{WB,\ MAX}$); to derive operating values for the prescribed flow rates $Q_{WB}$, $Q_P$, and $Q_{RF}$ such that the target post-procedure fraction of patient cells remaining (FCR), hematocrit ($H_{TF}$), and patient fluid volume change ($\Delta V$) are achieved simultaneously at the end of the procedure; and to maintain and or adjust these values in accordance with changing procedural conditions.

2. The system according to claim 1 wherein the controller is programmed to determine parameters M and F as follows:

$$M = 1 - \frac{\ln(FCR)}{\ln(1 + \Delta V/V_0)} \quad \Delta V \neq 0$$

and $$F = \frac{H_{T8}}{H_{T0}} \left[ \frac{FCR^{\frac{M}{M-1}} - 1}{FCR^{\frac{M}{M-1}} - \frac{H_{TF}}{H_{T0}}} \right] \quad \Delta V \neq 0$$

$$F = \frac{H_{T8}}{H_{T0}} \quad \Delta V = 0$$

and is further programmed to determine the prescribed flow rates as follows:

$$Q_{RF} = \frac{M}{F(M-1)} Q_{WB,MAX}.$$

$$Q_P = (F-1) Q_{RF}.$$

3. The system according to claim 1 wherein the controller is programmed to adjust the prescribed flow rates proportionally to not exceed an allowable citrate infusion rate and to maintain flow rate ratios that will simultaneously achieve the target post-procedure fraction of patient cells remaining (FCR), hematocrit ($H_{TF}$), and patient fluid volume change ($\Delta V$).

4. The system of claim 1 in which the controller is programmed to achieve the target post-procedure hematocrit $H_{TF}$ by linearly increasing the hematocrit of the replacement red blood cells introduced into the patient over the course of a red blood cell exchange procedure.

5. The system of claim 1 in which the controller is programmed to achieve the target post-procedure hematocrit $H_{TF}$ by exponentially increasing the hematocrit of the replacement red blood cells introduced into the patient over the course of a red blood cell exchange procedure.

6. The system of claim 1 further comprising a second source of replacement fluid and the controller is programmed to cease returning replacement fluid from the first source prior to introducing replacement fluid from the second source.

7. A blood processing system comprising:
a first flow path for flowing whole blood from a patient;
a separator communicating with the first flow path for separating at least red blood cells from plasma;
a second flow path communicating with the separator for flowing the separated plasma from the separator;
a third flow path communicating with the separator for flowing the separated red blood cells from the separator;
a flow controller associated with the second and third flow paths programmed to:
establish a target dilution hematocrit;
prompt an operator to select a first replacement fluid;
calculate an amount of whole blood to be processed to achieve the target dilution hematocrit;
process whole blood from a patient and return a first replacement fluid to the patient;
monitor the amount of whole blood processed or the procedure time to achieve the target dilution hematocrit; and continue to process the whole blood and return the first replacement fluid or a second replacement fluid to the patient to achieve a target end hematocrit.

8. The system of claim 7 wherein the controller is further programmed to prompt the user to select the first and second replacement fluid from one of saline, albumin, an albumin solution, and replacement red blood cells.

9. The system of claim 8 wherein the controller is further programmed to prompt the operator to enter the target dilution hematocrit.

10. The system of claim 9 in which the controller is programmed to achieve the target end hematocrit $H_{TF}$ by linearly increasing the hematocrit of the replacement red blood cells introduced into the patient over the course of a red blood cell exchange procedure.

11. The system of claim 9 in which the controller is programmed to achieve the target end hematocrit $H_{TF}$ by exponentially increasing the hematocrit of the replacement red blood cells introduced into the patient over the course of a red blood cell exchange procedure.

12. The system of claim 7 wherein the controller is further programmed:
- to calculate a volume of the first replacement fluid necessary to achieve the target dilution hematocrit;
- to display on a user interface an amount of the first replacement fluid returned to the patient; and
- to introduce the second replacement fluid to the patient when the amount of the first replacement fluid displayed on the user interface is equal to the calculated volume of the first replacement fluid necessary to achieve the target dilution hematocrit.

* * * * *